United States Patent
Su et al.

(10) Patent No.: US 9,060,745 B2
(45) Date of Patent: Jun. 23, 2015

(54) SYSTEM AND METHOD FOR DETECTING FLUID RESPONSIVENESS OF A PATIENT

(75) Inventors: Mark Su, Boulder, CO (US); James Nicholas Watson, Dunfermline (GB); Paul Stanley Addison, Edinburgh (GB)

(73) Assignee: Covidien LP, Mansfield, MA (US)

( * ) Notice: Subject to any disclaimer, the term of this patent is extended or adjusted under 35 U.S.C. 154(b) by 407 days.

(21) Appl. No.: 13/591,455

(22) Filed: Aug. 22, 2012

(65) Prior Publication Data

US 2014/0058229 A1    Feb. 27, 2014

(51) Int. Cl.
| | |
|---|---|
| *A61B 5/00* | (2006.01) |
| *A61B 5/024* | (2006.01) |
| *A61B 5/0245* | (2006.01) |
| *A61B 5/026* | (2006.01) |
| *A61B 5/1455* | (2006.01) |
| *A61B 5/1495* | (2006.01) |
| *A61B 6/00* | (2006.01) |

(Continued)

(52) U.S. Cl.
CPC ............. *A61B 5/7225* (2013.01); *A61B 5/7214* (2013.01); *A61B 6/507* (2013.01); *A61B 8/06* (2013.01); *A61B 5/0059* (2013.01); *A61B 5/02416* (2013.01); *A61B 5/0245* (2013.01); *A61B 5/026* (2013.01); *A61B 5/0432* (2013.01); *A61B 5/0507* (2013.01); *A61B 5/14552* (2013.01); *A61B 5/1495* (2013.01); *A61B 5/6826* (2013.01)

(58) Field of Classification Search
CPC ............... A61B 5/7214; A61B 5/0245; A61B 5/14552; A61B 5/026; A61B 6/507; A61B 5/0059; A61B 5/0507; A61B 5/7225; A61B 5/1495; A61B 5/02416

USPC .................................................. 600/323, 479
See application file for complete search history.

(56) References Cited

U.S. PATENT DOCUMENTS

| | | |
|---|---|---|
| 4,094,308 A | 6/1978 | Cormier |
| 4,282,655 A | 8/1981 | Tinman |

(Continued)

FOREIGN PATENT DOCUMENTS

| | | |
|---|---|---|
| EP | 0 537 383 | 4/1993 |
| EP | 0 841 034 | 5/1998 |

(Continued)

OTHER PUBLICATIONS

"Respiratory Variations in Pulse Oximetry Plethysmographic Waveform Amplitude to Predict Fluid Responsiveness in the Operating Room," Cannesson, et al., Anesthesiology vol. 106, No. 6, pp. 1105-1111.

(Continued)

*Primary Examiner* — Manuel Mendez
(74) *Attorney, Agent, or Firm* — Shvarts & Leiz LLP (57) ABSTRACT

A system is configured to determine a fluid responsiveness index of a patient from a physiological signal. The system may include a sensor configured to be secured to an anatomical portion of the patient, and a monitor operatively connected to the sensor. The sensor is configured to sense a physiological characteristic of the patient. The monitor is configured to receive a physiological signal from the sensor. The monitor may include an index-determining module configured to determine the fluid responsiveness index through formation of a ratio of one or both of amplitude or frequency modulation of the physiological signal to baseline modulation of the physiological signal.

20 Claims, 5 Drawing Sheets

(51) Int. Cl.
  *A61B 8/06* (2006.01)
  *A61B 5/0432* (2006.01)
  *A61B 5/05* (2006.01)

(56) References Cited

U.S. PATENT DOCUMENTS

| | | |
|---|---|---|
| 4,289,141 A | 9/1981 | Cormier |
| 4,450,527 A | 5/1984 | Sramek |
| 5,092,339 A | 3/1992 | Geddes |
| 5,178,151 A | 1/1993 | Sackner |
| 5,275,159 A | 1/1994 | Griebel |
| 5,331,960 A | 7/1994 | Krenzke |
| 5,408,327 A | 4/1995 | Geiler |
| 5,595,182 A | 1/1997 | Krivitski |
| 5,743,268 A | 4/1998 | Kabal |
| 5,817,010 A | 10/1998 | Hibl |
| 5,833,618 A | 11/1998 | Caro |
| 5,913,826 A | 6/1999 | Blank |
| 5,935,066 A | 8/1999 | Harris |
| 6,004,272 A | 12/1999 | Barry |
| 6,045,509 A | 4/2000 | Caro |
| 6,155,984 A | 12/2000 | Krivitski |
| 6,292,686 B1 | 9/2001 | Chaiken |
| 6,371,921 B1 | 4/2002 | Caro |
| 6,389,306 B1 | 5/2002 | Chaiken |
| 6,503,206 B1 | 1/2003 | Li |
| 6,616,613 B1 | 9/2003 | Goodman |
| 6,719,705 B2 | 4/2004 | Mills |
| 6,740,072 B2 | 5/2004 | Starkweather |
| 6,754,523 B2 | 6/2004 | Toole |
| 6,758,822 B2 | 7/2004 | Romano |
| 6,760,608 B2 | 7/2004 | Lynn |
| 6,776,764 B2 | 8/2004 | Pinsky |
| 6,816,266 B2 | 11/2004 | Varshneya |
| 6,869,402 B2 | 3/2005 | Arnold |
| 6,875,176 B2 | 4/2005 | Mourad |
| 7,022,077 B2 | 4/2006 | Mourad |
| 7,033,320 B2 | 4/2006 | Von Behren |
| 7,056,292 B2 | 6/2006 | Hutchinson |
| 7,171,271 B2 | 1/2007 | Koh |
| 7,220,230 B2 | 5/2007 | Roteliuk |
| 7,452,333 B2 | 11/2008 | Roteliuk |
| 7,462,152 B2 | 12/2008 | Kolluri |
| 7,615,011 B2 | 11/2009 | Sugo |
| 7,674,231 B2 | 3/2010 | McCombie |
| 7,704,209 B2 | 4/2010 | Bennett |
| 7,747,301 B2 | 6/2010 | Cheng |
| 7,785,263 B2 | 8/2010 | Roteliuk |
| 7,806,830 B2 | 10/2010 | Bernstein |
| 7,850,617 B2 | 12/2010 | Goedje |
| 7,881,762 B2 | 2/2011 | Kling |
| 7,894,869 B2 | 2/2011 | Hoaran |
| 7,899,510 B2 | 3/2011 | Hoaran |
| 7,976,472 B2 | 7/2011 | Kiani |
| 8,073,516 B2 | 12/2011 | Scharf |
| 8,073,518 B2 | 12/2011 | Chin |
| 8,187,197 B2 | 5/2012 | Shapira |
| 8,211,031 B2 | 7/2012 | Poupko |
| 2002/0022785 A1 | 2/2002 | Romano |
| 2002/0082485 A1 | 6/2002 | Faithfull |
| 2003/0167012 A1 | 9/2003 | Friedman |
| 2005/0080345 A1 | 4/2005 | Finburgh |
| 2005/0085707 A1 | 4/2005 | Korsten |
| 2005/0124903 A1 | 6/2005 | Roteliuk |
| 2005/0240087 A1 | 10/2005 | Keenan |
| 2006/0184051 A1 | 8/2006 | Hempstead |
| 2006/0224053 A1 | 10/2006 | Black |
| 2007/0093702 A1 | 4/2007 | Yu |
| 2007/0213625 A1 | 9/2007 | Nayak |
| 2007/0249949 A1 | 10/2007 | Hadley |
| 2008/0082004 A1 | 4/2008 | Banet |
| 2008/0119329 A1 | 5/2008 | Punkka |
| 2008/0139958 A1 | 6/2008 | Uemura |
| 2008/0183232 A1 | 7/2008 | Voss |
| 2008/0287815 A1 | 11/2008 | Chon |
| 2009/0099459 A1 | 4/2009 | Svanberg |
| 2009/0149762 A1 | 6/2009 | Yang |
| 2009/0177110 A1 | 7/2009 | Lyden |
| 2009/0198140 A1 | 8/2009 | Aboy |
| 2009/0204012 A1 | 8/2009 | Joeken |
| 2009/0240119 A1 | 9/2009 | Schwaibold |
| 2009/0326353 A1 | 12/2009 | Watson |
| 2009/0326388 A1 | 12/2009 | Watson |
| 2009/0326395 A1 | 12/2009 | Watson |
| 2010/0016739 A1 | 1/2010 | Shelley |
| 2010/0049007 A1 | 2/2010 | Sterling |
| 2010/0049071 A1 | 2/2010 | Goor |
| 2010/0081895 A1 | 4/2010 | Zand |
| 2010/0152547 A1 | 6/2010 | Sterling |
| 2010/0152591 A1 | 6/2010 | Yu |
| 2010/0160794 A1 | 6/2010 | Banet |
| 2010/0191128 A1 | 7/2010 | Shelley |
| 2010/0210924 A1 | 8/2010 | Parthasarathy |
| 2010/0249542 A1 | 9/2010 | Thijs |
| 2010/0249559 A1 | 9/2010 | Lovejoy |
| 2010/0249612 A1 | 9/2010 | Cohen |
| 2010/0268090 A1 | 10/2010 | Rubinstein |
| 2010/0268101 A1 | 10/2010 | Sugo |
| 2010/0268518 A1 | 10/2010 | Sugo |
| 2010/0298689 A1 | 11/2010 | Wang |
| 2010/0324388 A1 | 12/2010 | Moon |
| 2010/0324431 A1 | 12/2010 | Addison |
| 2010/0324827 A1 | 12/2010 | Addison |
| 2011/0009754 A1 | 1/2011 | Wenzel |
| 2011/0009755 A1 | 1/2011 | Wenzel |
| 2011/0026784 A1 | 2/2011 | Van Slyke |
| 2011/0034813 A1 | 2/2011 | Cohen |
| 2011/0040345 A1 | 2/2011 | Wenzel |
| 2011/0060234 A1 | 3/2011 | Zhou |
| 2011/0060531 A1 | 3/2011 | Sugo |
| 2011/0077532 A1 | 3/2011 | Kim |
| 2011/0087115 A1 | 4/2011 | Sackner |
| 2011/0098112 A1 | 4/2011 | LeBoeuf |
| 2011/0098546 A1 | 4/2011 | Farazi |
| 2011/0105918 A1 | 5/2011 | Fortin |
| 2011/0172504 A1 | 7/2011 | Wegerich |
| 2011/0209915 A1 | 9/2011 | Telfort |
| 2011/0224564 A1 | 9/2011 | Moon |
| 2011/0270097 A1 | 11/2011 | Aboy |
| 2011/0301436 A1 | 12/2011 | Teixeira |
| 2012/0022350 A1 | 1/2012 | Teixeira |
| 2012/0029320 A1 | 2/2012 | Watson |
| 2012/0029361 A1 | 2/2012 | Addison |
| 2012/0029363 A1 | 2/2012 | Lund |
| 2012/0046557 A1 | 2/2012 | Kiani |
| 2012/0053433 A1 | 3/2012 | Chamoun |
| 2012/0053469 A1 | 3/2012 | Melker |
| 2012/0065485 A1 | 3/2012 | Benni |
| 2012/0065527 A1 | 3/2012 | Gill |
| 2012/0065528 A1 | 3/2012 | Gill |
| 2012/0078069 A1 | 3/2012 | Melker |
| 2012/0109018 A1 | 5/2012 | Gertner |
| 2012/0136261 A1 | 5/2012 | Sethi |
| 2012/0172723 A1 | 7/2012 | Gertner |
| 2012/0172732 A1 | 7/2012 | Gertner |

FOREIGN PATENT DOCUMENTS

| | | |
|---|---|---|
| EP | 1 443 856 | 2/2006 |
| EP | 1 769 737 | 4/2007 |
| EP | 1 884 189 | 2/2008 |
| EP | 2 281 508 | 2/2011 |
| EP | 2 047 794 | 2/2012 |
| EP | 2 217 140 | 2/2012 |
| WO | WO 91/13589 | 9/1991 |
| WO | WO 94/14372 | 7/1994 |
| WO | WO 97/47236 | 12/1997 |
| WO | WO 98/41279 | 9/1998 |
| WO | WO 02/03076 | 1/2002 |
| WO | WO 03/082099 | 10/2003 |
| WO | WO 2004/071292 | 8/2004 |
| WO | WO 2005/055825 | 6/2005 |
| WO | WO 2006/100676 | 9/2006 |
| WO | WO 2007/109065 | 9/2007 |

(56) References Cited

FOREIGN PATENT DOCUMENTS

| | | |
|---|---|---|
| WO | WO 2008/094598 | 8/2008 |
| WO | WO 2008/144404 | 11/2008 |
| WO | WO 2008/144525 | 11/2008 |
| WO | WO 2009/009761 | 1/2009 |
| WO | WO 2009/014420 | 1/2009 |
| WO | WO 2009/101140 | 8/2009 |
| WO | WO 2010/001231 | 1/2010 |
| WO | WO 2010/045556 | 4/2010 |
| WO | WO 2011/080190 | 7/2010 |
| WO | WO 2010/096475 | 8/2010 |
| WO | WO 2010/111073 | 9/2010 |
| WO | WO/2010/124034 | 10/2010 |
| WO | WO 2010/146326 | 12/2010 |
| WO | WO 2010/146327 | 12/2010 |
| WO | WO 2011/047211 | 4/2011 |
| WO | WO 2011/050066 | 4/2011 |
| WO | WO 2011/051822 | 5/2011 |
| WO | WO 2011/060220 | 5/2011 |
| WO | WO 2011/077294 | 6/2011 |
| WO | WO 2011/080194 | 7/2011 |
| WO | WO2011/087927 | 7/2011 |
| WO | WO 2011/089488 | 7/2011 |
| WO | WO 2012/009350 | 1/2012 |
| WO | WO 2012/014065 | 2/2012 |
| WO | WO 2012/015426 | 2/2012 |
| WO | WO 2012/027613 | 3/2012 |
| WO | WO 2012/032413 | 3/2012 |
| WO | WO 2012/032536 | 3/2012 |
| WO | WO 2012/052926 | 4/2012 |
| WO | WO 2012/075322 | 6/2012 |
| WO | WO 2012/076957 | 6/2012 |

OTHER PUBLICATIONS

International Search Report and Written Opinion of the International Searching Authority for counterpart PCT application PCT/SU2013/056179.

"Derivation of Respiratory Signals from Multi-lead ECGS, Moody," et al. (1985).

"Photoplethsmography and its application in clinical physiological measurement," Physiol. Meas. 28 (2007).

"Venus Oximetry," Signa Vitae 2007.

"Near-Infrared Spectrometry (NIRS) and Venous-side Monitoring of the Circulation," Hoffman.

"On the Analysis of Fingertip Photoplethysmogram Signals," Elgendi, Current Cardiology Reviews, 2012.

"A Computer Based Photoplethysmographic Vascular Analyzer Through Derivatives," Gonzalez, et al, Computers in Cardiology (2008).

"Noninvasive Assessment of the Digital Volume Pulse: Comparison with the Peripheral Pressure Pulse," Millasseau, et al., Journal of the American Heart Association (2000).

"Non-Invasive Estimation of Cardiac Output from Finger Photoplethysmogram Based on Windkessel Model," Poon, Bulletin of Advance Technology Research, vol. 4, No. 6 (2010).

"Non-constrained Blood Pressure Monitoring Using ECG and PPG for Personal Healthcare," Yoon, et al, (2008).

"How to measure heart rate?" Vogel, et al. Eur. J. Clin Paramacol (2004) 60.461-466.

"Resting Heart Rate in Cardiovascular Disease," Fox, et al. Journal of the Amercan College of Cardiology vol. 50, No. 9 (2007).

"Why measure resting heart rate?" Nauman (2012).

"The shape and dimensions of photoplethsymographic pulse waves; a measurement repeatability study," Marcinkevics, et al. Acta Universitatis Latviensis,vol. 753, Bilology, pp. 99-106 (2009).

"Monitoring of Reactive Hyperemia Using Photoplethysmographic Pulse Amplitude and Transit Time," Selvavaj, et al. Journal of Clinical Monitoring and Computing 23:315-322 (2009).

"Photoacoustic thermal diffusion flowmetry," Sheinfeld, et al., Biomedical Optics Express vol. 3, No. 4 (2012).

"Flow dependent photothermal modulation of the photacoustic response," Sheinfeld, et al, Photonos Plus Ultrasound: Imaging and Sensing (2012).

"Relation between repiratory variations in pulse oximetry plethysmographic waveform amplitude and arterial pulse pressure in ventilated patients," Cannesson, et al. Ciritical Care (2005).

"Pulse oximeter plethysmograph variation and its relationship to the arterial waveform in mechanically ventilated childer," Chandler, et al. J. Clin. Monit. Comput. (2012).

"Variations in Arterial Blood Pressure and Photoplethysmography During Mechanical Ventilation," Natalani, et al., Technology, Computing, and Simulation, vol. 103, No. 5, (2006).

SYSTEM AND METHOD FOR DETECTING FLUID RESPONSIVENESS OF A PATIENT

FIELD

Embodiments of the present disclosure generally relate to physiological signal processing and more particularly, to processing physiological signals to determine the fluid responsiveness of a patient.

BACKGROUND

Photoplethysmography (PPG) is a non-invasive, optical measurement that may be used to detect changes in blood volume within tissue, such as skin, of an individual. PPG may be used with pulse oximeters, vascular diagnostics, and digital blood pressure detection systems. Typically, a PPG system includes a light source that is used to illuminate tissue of a patient. A photodetector is then used to measure small variations in light intensity associated with blood volume changes proximal to the illuminated tissue.

In general, a PPG signal is a physiological signal that includes an AC physiological component related to cardiac synchronous changes in the blood volume with each heartbeat. The AC component is typically superimposed on a DC baseline that may be related to respiration, sympathetic nervous system activity, and thermoregulation.

SUMMARY

Certain embodiments provide a system for determining a fluid responsiveness index of a patient from a physiological signal, such as a PPG signal. The system may include a sensor configured to be secured to an anatomical portion of the patient, and a monitor operatively connected to the sensor. The sensor is configured to sense a physiological characteristic of the patient. The monitor is configured to receive a physiological signal from the sensor. The monitor includes an index-determining module configured to determine the fluid responsiveness index through formation of a ratio of one or both of amplitude modulation or frequency modulation of the physiological signal with respect to baseline modulation of the physiological signal.

The monitor may include a normalization module configured to normalize the fluid responsiveness index. The normalization module may be configured to normalize the fluid responsiveness index to correct for changes in one or both of vascular tone or motion artifacts. The normalization module may be configured to normalize the fluid responsiveness index based on one or more of a relative amplitude ratio of the physiological signal, a width of at least one primary peak of the physiological signal, a time difference between the at least one primary peak and at least one trailing peak, or a pleth modulation ratio of the physiological signal.

The index-determining module may determine the fluid responsiveness index by applying a calibration coefficient or constant to the ratio.

The physiological signal may include a photoplethysmogram (PPG) signal. The sensor may include a PPG sensor. The monitor may include a PPG monitor. The sensor may include a pulse oximetry sensor. The monitor may include a pulse oximetry monitor.

The system may also include a fluid delivery device operatively connected to the monitor. The monitor may automatically determine whether or not to administer fluid to a patient from the fluid delivery device based on the fluid responsiveness index.

Certain embodiments provide a method for determining a fluid responsiveness index of a patient from a physiological signal. The method may include securing a sensor to an anatomical portion of the patient, sensing a physiological characteristic of the patient with the sensor, receiving a physiological signal from the sensor at a monitor comprising an index-determining module, and determining the fluid responsiveness index with the index-determining module. The determining the fluid responsiveness index operation may include forming a ratio of one or both of amplitude modulation or frequency modulation of the physiological signal with respect to baseline modulation of the physiological signal.

Certain embodiments provide a tangible and non-transitory computer readable medium that includes one or more sets of instructions configured to direct a computer to receive a physiological signal from a sensor secured to an anatomical portion of a patient, and determine a fluid responsiveness index of a patient by forming a ratio of one or both of amplitude modulation or frequency modulation of the physiological signal with respect to baseline modulation of the physiological signal.

Embodiments of the present disclosure allow for quick and simple determination of fluid responsiveness through analysis of a physiological signal, such as a PPG signal. In contrast to previous systems and methods, embodiments may not require an arterial line ("A-line") having a pressure transducer to detect fluid responsiveness. Moreover, embodiments may be used to detect fluid responsiveness with patients that are spontaneously breathing and/or those that are on lung-protective low-tidal volume ventilation, in contrast to previous systems and methods that typically require high-tidal ventilation in order to determine fluid responsiveness. Further, embodiments provide systems and methods for normalizing a basic fluid responsiveness index or value, such as by accounting for changes in vascular tone and/or motion artifacts.

Certain embodiments may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

DETAILED DESCRIPTION

Figure 1:
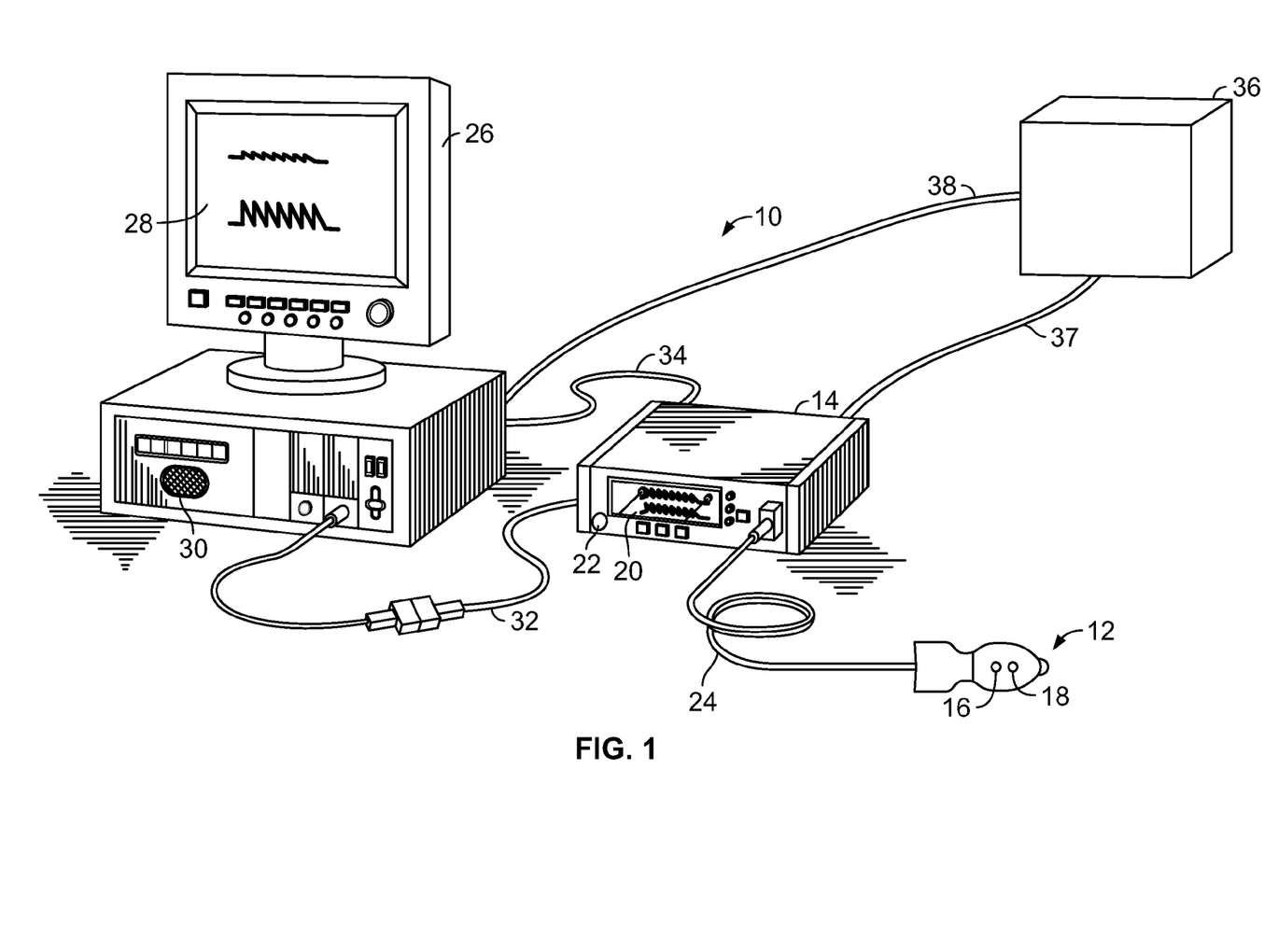
FIG. 1 illustrates an isometric view of a photoplethysmogram (PPG) system, according to an embodiment.

FIG. 1 illustrates an isometric view of a PPG system 10, according to an embodiment. While the system 10 is shown and described as a PPG system 10, the system may be various other types of physiological detection systems, such as an electrocardiogram system, a phonocardiogram system, and the like. The PPG system 10 may be a pulse oximetry system, for example. The system 10 may include a PPG sensor 12 and a PPG monitor 14. The PPG sensor 12 may include an emitter 16 configured to emit light into tissue of a patient. For example, the emitter 16 may be configured to emit light at two or more wavelengths into the tissue of the patient. The PPG sensor 12 may also include a detector 18 that is configured to detect the emitted light from the emitter 16 that emanates from the tissue after passing through the tissue.

The system 10 may include a plurality of sensors forming a sensor array in place of the PPG sensor 12. Each of the sensors of the sensor array may be a complementary metal oxide semiconductor (CMOS) sensor, for example. Alternatively, each sensor of the array may be a charged coupled device (CCD) sensor. In another embodiment, the sensor array may include a combination of CMOS and CCD sensors. The CCD sensor may include a photoactive region and a transmission region configured to receive and transmit, while the CMOS sensor may include an integrated circuit having an array of pixel sensors. Each pixel may include a photodetector and an active amplifier.

The emitter 16 and the detector 18 may be configured to be located at opposite sides of a digit, such as a finger or toe, in which case the light that is emanating from the tissue passes completely through the digit. The emitter 16 and the detector 18 may be arranged so that light from the emitter 16 penetrates the tissue and is reflected by the tissue into the detector 18, such as a sensor designed to obtain pulse oximetry data.

The sensor 12 or sensor array may be operatively connected to and draw power from the monitor 14. Optionally, the sensor 12 may be wirelessly connected to the monitor 14 and include a battery or similar power supply (not shown). The monitor 14 may be configured to calculate physiological parameters based at least in part on data received from the sensor 12 relating to light emission and detection. Alternatively, the calculations may be performed by and within the sensor 12 and the result of the oximetry reading may be passed to the monitor 14. Additionally, the monitor 14 may include a display 20 configured to display the physiological parameters or other information about the system 10. The monitor 14 may also include a speaker 22 configured to provide an audible sound that may be used in various other embodiments, such as for example, sounding an audible alarm in the event that physiological parameters are outside a predefined normal range.

The sensor 12, or the sensor array, may be communicatively coupled to the monitor 14 via a cable 24. Alternatively, a wireless transmission device (not shown) or the like may be used instead of, or in addition to, the cable 24.

The system 10 may also include a multi-parameter workstation 26 operatively connected to the monitor 14. The workstation 26 may be or include a computing sub-system 30, such as standard computer hardware. The computing sub-system 30 may include one or more modules and control units, such as processing devices that may include one or more microprocessors, microcontrollers, integrated circuits, memory, such as read-only and/or random access memory, and the like. The workstation 26 may include a display 28, such as a cathode ray tube display, a flat panel display, such as a liquid crystal display (LCD), light-emitting diode (LED) display, a plasma display, or any other type of monitor. The computing sub-system 30 of the workstation 26 may be configured to calculate physiological parameters and to show information from the monitor 14 and from other medical monitoring devices or systems (not shown) on the display 28. For example, the workstation 26 may be configured to display an estimate of a patient's blood oxygen saturation generated by the monitor 14 (referred to as an $SpO_2$ measurement), pulse rate information from the monitor 14 and blood pressure from a blood pressure monitor (not shown) on the display 28.

The monitor 14 may be communicatively coupled to the workstation 26 via a cable 32 and/or 34 that is coupled to a sensor input port or a digital communications port, respectively and/or may communicate wirelessly with the workstation 26. Additionally, the monitor 14 and/or workstation 26 may be coupled to a network to enable the sharing of information with servers or other workstations. The monitor 14 may be powered by a battery or by a conventional power source such as a wall outlet.

The system 10 may also include a fluid delivery device 36 that is configured to deliver fluid to a patient. The fluid delivery device 36 may be an intravenous line, an infusion pump, any other suitable fluid delivery device, or any combination thereof that is configured to deliver fluid to a patient. The fluid delivered to a patient may be saline, plasma, blood, water, any other fluid suitable for delivery to a patient, or any combination thereof. The fluid delivery device 36 may be configured to adjust the quantity or concentration of fluid delivered to a patient.

The fluid delivery device 36 may be communicatively coupled to the monitor 14 via a cable 37 that is coupled to a digital communications port or may communicate wirelessly with the workstation 26. Alternatively, or additionally, the fluid delivery device 36 may be communicatively coupled to the workstation 26 via a cable 38 that is coupled to a digital communications port or may communicate wirelessly with the workstation 26.

Figure 2:
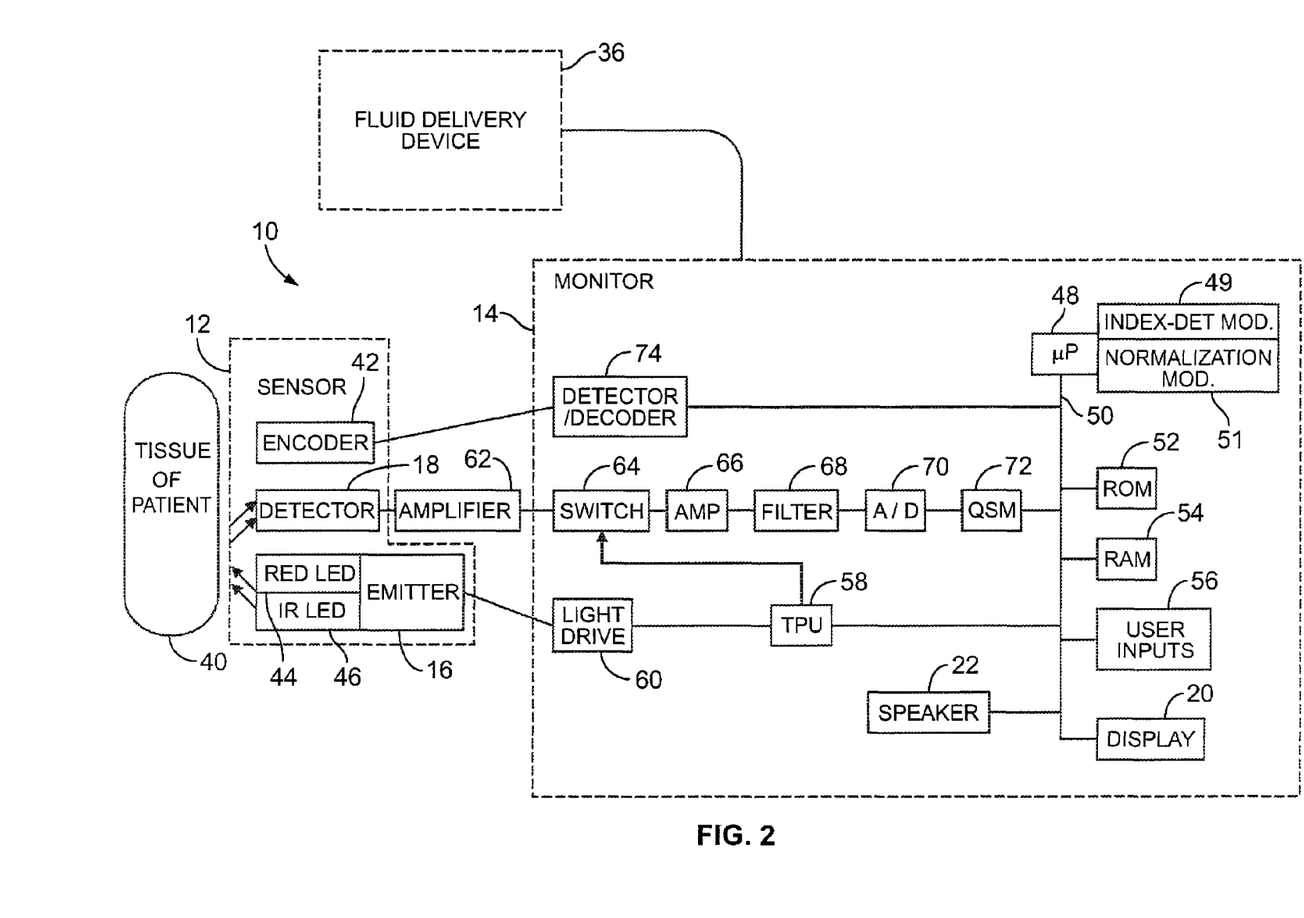
FIG. 2 illustrates a simplified block diagram of a PPG system, according to an embodiment.

FIG. 2 illustrates a simplified block diagram of the PPG system 10, according to an embodiment. When the PPG system 10 is a pulse oximetry system, the emitter 16 may be configured to emit at least two wavelengths of light (for example, red and infrared) into tissue 40 of a patient. Accordingly, the emitter 16 may include a red light-emitting light source such as a red light-emitting diode (LED) 44 and an infrared light-emitting light source such as an infrared LED 46 for emitting light into the tissue 40 at the wavelengths used to calculate the patient's physiological parameters. For example, the red wavelength may be between about 600 nm and about 700 nm, and the infrared wavelength may be between about 800 nm and about 1000 nm. In embodiments where a sensor array is used in place of single sensor, each sensor may be configured to emit a single wavelength. For example, a first sensor may emit a red light while a second sensor may emit an infrared light.

As discussed above, the PPG system 10 is described in terms of a pulse oximetry system. However, the PPG system 10 may be various other types of systems. For example, the PPG system 10 may be configured to emit more or less than two wavelengths of light into the tissue 40 of the patient. Further, the PPG system 10 may be configured to emit wavelengths of light other than red and infrared into the tissue 40. As used herein, the term "light" may refer to energy produced by radiative sources and may include one or more of ultrasound, radio, microwave, millimeter wave, infrared, visible, ultraviolet, gamma ray or X-ray electromagnetic radiation. The light may also include any wavelength within the radio, microwave, infrared, visible, ultraviolet, or X-ray spectra, and that any suitable wavelength of electromagnetic radiation may be used with the system 10. The detector 18 may be configured to be specifically sensitive to the chosen targeted energy spectrum of the emitter 16.

The detector 18 may be configured to detect the intensity of light at the red and infrared wavelengths. Alternatively, each sensor in the array may be configured to detect an intensity of a single wavelength. In operation, light may enter the detector 18 after passing through the tissue 40. The detector 18 may convert the intensity of the received light into an electrical signal. The light intensity may be directly related to the absorbance and/or reflectance of light in the tissue 40. For example, when more light at a certain wavelength is absorbed or reflected, less light of that wavelength is received from the tissue by the detector 18. After converting the received light to an electrical signal, the detector 18 may send the signal to the monitor 14, which calculates physiological parameters based on the absorption of the red and infrared wavelengths in the tissue 40.

In an embodiment, an encoder 42 may store information about the sensor 12, such as sensor type (for example, whether the sensor is intended for placement on a forehead or digit) and the wavelengths of light emitted by the emitter 16. The stored information may be used by the monitor 14 to select appropriate algorithms, lookup tables and/or calibration coefficients stored in the monitor 14 for calculating physiological parameters of a patient. The encoder 42 may store or otherwise contain information specific to a patient, such as, for example, the patient's age, weight, and diagnosis. The information may allow the monitor 14 to determine, for example, patient-specific threshold ranges related to the patient's physiological parameter measurements, and to enable or disable additional physiological parameter algorithms. The encoder 42 may, for instance, be a coded resistor that stores values corresponding to the type of sensor 12 or the types of each sensor in the sensor array, the wavelengths of light emitted by emitter 16 on each sensor of the sensor array, and/or the patient's characteristics. Optionally, the encoder 42 may include a memory in which one or more of the following may be stored for communication to the monitor 14: the type of the sensor 12, the wavelengths of light emitted by emitter 16, the particular wavelength each sensor in the sensor array is monitoring, a signal threshold for each sensor in the sensor array, any other suitable information, or any combination thereof.

Signals from the detector 18 and the encoder 42 may be transmitted to the monitor 14. The monitor 14 may include a general-purpose control unit, such as a microprocessor 48 connected to an internal bus 50. The microprocessor 48 may be configured to execute software, which may include an operating system and one or more applications, as part of performing the functions described herein. A read-only memory (ROM) 52, a random access memory (RAM) 54, user inputs 56, the display 20, and the speaker 22 may also be operatively connected to the bus 50. The control unit and/or the microprocessor 48 may include an index-determining module 49 that is configured to determine a basic fluid responsiveness index or value, as described below, and a normalization module 51 that is configured to normalize the basic fluid responsiveness index or value based on changes in vascular tone, as described below.

The RAM 54 and the ROM 52 are illustrated by way of example, and not limitation. Any suitable computer-readable media may be used in the system for data storage. Computer-readable media are configured to store information that may be interpreted by the microprocessor 48. The information may be data or may take the form of computer-executable instructions, such as software applications, that cause the microprocessor to perform certain functions and/or computer-implemented methods. The computer-readable media may include computer storage media and communication media. The computer storage media may include volatile and non-volatile media, removable and non-removable media implemented in any method or technology for storage of information such as computer-readable instructions, data structures, program modules or other data. The computer storage media may include, but are not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which may be used to store desired information and that may be accessed by components of the system.

The monitor 14 may also include a time processing unit (TPU) 58 configured to provide timing control signals to a light drive circuitry 60, which may control when the emitter 16 is illuminated and multiplexed timing for the red LED 44 and the infrared LED 46. The TPU 58 may also control the gating-in of signals from the detector 18 through an amplifier 62 and a switching circuit 64. The signals are sampled at the proper time, depending upon which light source is illuminated. The received signal from the detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In an embodiment, there may be multiple separate parallel paths having amplifier 66, filter 68, and ND converter 70 for multiple light wavelengths or spectra received.

The microprocessor 48 may be configured to determine the patient's physiological parameters, such as $SpO_2$ and pulse rate, using various algorithms and/or look-up tables based on the value(s) of the received signals and/or data corresponding to the light received by the detector 18. The signals corresponding to information about a patient, and regarding the intensity of light emanating from the tissue 40 over time, may be transmitted from the encoder 42 to a decoder 74. The transmitted signals may include, for example, encoded information relating to patient characteristics. The decoder 74 may translate the signals to enable the microprocessor 48 to determine the thresholds based on algorithms or look-up tables stored in the ROM 52. The user inputs 56 may be used to enter information about the patient, such as age, weight, height, diagnosis, medications, treatments, and so forth. The display 20 may show a list of values that may generally apply to the patient, such as, for example, age ranges or medication families, which the user may select using the user inputs 56.

The fluid delivery device 36 may be communicatively coupled to the monitor 14. The microprocessor 48 may determine the patient's physiological parameters, such as a change or level of fluid responsiveness, and display the parameters on the display 20. In an embodiment, the parameters determined by the microprocessor 48 or otherwise by the monitor 14 may be used to adjust the fluid delivered to the patient via fluid delivery device 36.

As noted, the PPG system 10 may be a pulse oximetry system. A pulse oximeter is a medical device that may determine oxygen saturation of blood. The pulse oximeter may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of a patient. Pulse oximeters typically measure and display various blood flow characteristics including, but not limited to, the oxygen saturation of hemoglobin in arterial blood.

A pulse oximeter may include a light sensor, similar to the sensor 12, that is placed at a site on a patient, typically a fingertip, toe, forehead or earlobe, or in the case of a neonate, across a foot. The pulse oximeter may pass light using a light source through blood perfused tissue and photoelectrically sense the absorption of light in the tissue. For example, the pulse oximeter may measure the intensity of light that is received at the light sensor as a function of time. A signal representing light intensity versus time or a mathematical manipulation of this signal (for example, a scaled version thereof, a log taken thereof, a scaled version of a log taken thereof, and/or the like) may be referred to as the photoplethysmograph (PPG) signal. In addition, the term "PPG signal," as used herein, may also refer to an absorption signal (for example, representing the amount of light absorbed by the tissue) or any suitable mathematical manipulation thereof. The light intensity or the amount of light absorbed may then be used to calculate the amount of the blood constituent (for example, oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with lower oxygen saturation. By comparing the intensities of two wavelengths at different points in the pulse cycle, it is possible to estimate the blood oxygen saturation of hemoglobin in arterial blood.

The PPG system 10 and pulse oximetry are further described in United States Patent Application Publication No. 2012/0053433, entitled "System and Method to Determine $SpO_2$ Variability and Additional Physiological Parameters to Detect Patient Status," United States Patent Application Publication No. 2010/0324827, entitled "Fluid Responsiveness Measure," and United States Patent Application Publication No. 2009/0326353, entitled "Processing and Detecting Baseline Changes in Signals," all of which are hereby incorporated by reference in their entireties.

Respiratory variation of the PPG signal may correlate with fluid responsiveness. Fluid responsiveness relates to the volume of fluid, such as blood, in the arteries, veins, and vasculature of an individual. In general, fluid responsiveness may include a measurement of the response of stroke volume, the volume of blood passing out of the heart with each heartbeat, to venous return, the volume of blood entering the heart with each heartbeat, caused by the clinical administration of fluid into the vasculature, such as through an intravenous injection. With each heartbeat, a certain amount of blood is pumped out of the heart. The more blood that fills the heart, the more blood the heart can pump out with each heartbeat. If blood volume is too low, the heart may not fully fill with blood. Therefore, the heart may not pump out as much blood with each heartbeat. Consequently, low blood volume may lead to low blood pressure, and organs and tissues may not receive enough blood to optimally and/or properly function. Monitoring fluid responsiveness allows a physician to determine whether additional fluid should be provided to a patient, such as through an intravenous fluid injection. In short fluid responsiveness represents a prediction of whether or not additional intravenous fluid may improve blood flow within a patient. Fluid responsiveness may be viewed as a response of a heart in relation to overall fluid within a patient.

Fluid responsiveness may be monitored in, for example, critically-ill patients because fluid administration plays an important role in optimizing stroke volume, cardiac output, and oxygen delivery to organs and tissues. However, clinicians need to balance central blood volume depletion and volume overloading. Critically-ill patients are generally at greater risk for volume depletion and severe hypotension is a common life-threatening condition in critically-ill patients. Conversely, administering too much fluid may induce life-threatening adverse effects, such as volume overload, systemic and pulmonary edema, and increased tissue hypoxia. Therefore, obtaining reliable information and parameters that aid clinicians in fluid management decisions may help improve patient outcomes.

Figure 3:
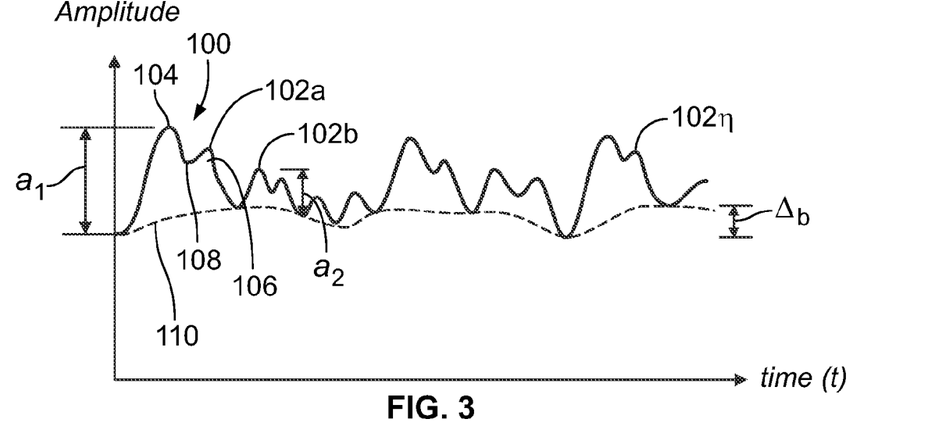
FIG. 3 illustrates a PPG signal over time, according to an embodiment.

FIG. 3 illustrates a PPG signal 100 over time, according to an embodiment. The PPG signal 100 is an example of a physiological signal. However, embodiments may be used in relation to various other physiological signals, such as electrocardiogram signals, phonocardiogram signals, ultrasound signals, and the like. The PPG signal 100 may be determined, formed, and displayed as a waveform by the monitor 14 (shown in FIG. 1) that receives signal data from the PPG sensor 12 (shown in FIG. 1). For example, the monitor 14 may receive signals from the PPG sensor 12 positioned on a finger of a patient. The monitor 14 processes the received signals, and displays the resulting PPG signal 100 on the display 28 (shown in FIG. 1).

The PPG signal 100 may include a plurality of pulses 102a-102n over a predetermined time period. The time period may be a fixed time period, or the time period may be variable. Moreover, the time period may be a rolling time period, such as a 5 second rolling timeframe.

Each pulse 102a-102n may represent a single heartbeat and may include a pulse-transmitted or primary peak 104 separated from a pulse-reflected or trailing peak 106 by a dichrotic notch 108. The primary peak 104 represents a pressure wave generated from the heart to the point of detection, such as in a finger where the PPG sensor 12 (shown in FIG. 1) is positioned. The trailing peak 106 may represent a pressure wave that is reflected from the location proximate where the PPG sensor 12 is positioned back toward the heart.

As shown in FIG. 3, each pulse 102a-102n has a particular amplitude. For example, the pulse 102a has an amplitude $a_1$, while the pulse 102b has an amplitude $a_2$. The amplitudes $a_1$ and $a_2$ may differ, as shown. Indeed, the amplitudes of each pulse 102a-102n may vary with respect to one another. In general, the overall amplitude of the PPG signal 100 over time t may modulate. The index-determining module 49 (shown in FIG. 2) of the monitor 14 may track and store the magnitude of the amplitude modulation of the PPG signal 100 over time t. Optionally, the index-determining module 49 of the monitor 14 may track and store the magnitude of the amplitude modulation of the PPG signal 100 over time periods of varying lengths. For example, the index-determining module 49 of the monitor 14 may compare the amplitudes of neighboring pulses 102a and 102b and store the change in amplitude between the two pulses 102a and 102b as a magnitude of amplitude modulation. The index-determining module 49 of the monitor 14 may continually track and store amplitude modulation between neighboring pulses 102a-102n over the time period t. Optionally, the index-determining module 49 of the monitor 14 may determine an average modulation of the pulses 102a-102n over the time period t and store the average modulation as a magnitude of amplitude modulation.

The PPG signal 100 also includes a baseline 110, which may modulate over the time period t. The index-determining module 49 of the monitor 14 may monitor and store the baseline modulation $\Delta b$ over the time period t. Optionally, the index-determining module 49 of the monitor 14 may determine the baseline modulation between neighboring peaks 102a-102n. As shown in FIG. 3, however, the magnitude of baseline modulation Δb may be summed or averaged over the time period t.

The index-determining module 49 of the monitor 14 may determine an index of fluid responsiveness determined through the modulation of the PPG signal. For example, the index of fluid responsiveness may be determined through a ratio of amplitude modulation to baseline modulation (AM/BM). The amplitude modulation and baseline modulation may be calculated and/or otherwise determined by the index-determining module 49 or otherwise by the monitor 14 as discussed above.

It has been found that amplitude modulation relates to stroke volume. For example, amplitude modulation may be directly proportional to stroke volume. The higher the magnitude of amplitude modulation, the higher the stroke volume.

Similarly, it has been found that baseline modulation relates to venous return. For example, baseline modulation may be directly proportional to venous return. The higher the magnitude of baseline modulation, the higher the venous return.

The ratio of amplitude modulation to baseline modulation (AM/BM) provides an index of fluid responsiveness.

$$BFR = c(AM/BM) \quad (1)$$

where BFR is Basic Fluid Responsiveness or a fluid responsiveness index, AM is amplitude modulation, BM is baseline modulation, and c represents an empirically-determined constant and/or calibration coefficient. The empirically-determined constant c may be a calibration value that may be determined through clinical examinations of patients. For example, a group of patients may be monitored to determine fluid responsiveness levels through traditional detection methods, such as with pressure transducers secured to arterial catheters. The traditional detection methods yield fluid responsiveness values that are correlated with particular AM and BM, which may also be monitored at the same time. The empirically-determined constant c may then be based on the relation between the fluid responsiveness values and AM and BM. The calibrated value c may then be used by the index-determining module 49 of the monitor 14 with respect to a determination of basic fluid responsiveness in other patients based on detection of AM and BM. The index-determining module 49 of the monitor 14 may store and use the value c as a calibration coefficient, and/or in relation to a look-up table. Optionally, the BFR may be determined simply through the ratio of AM/BM. Thus, the BFR or fluid responsiveness index may include the ratio of AM/BM and the empirically-determined coefficient c. As shown above, the BFR or fluid responsiveness index may be a product of the ratio of AM/BM and the empirically-determined coefficient c.

The BFR may be a dimensionless scalar index value. Based on Equation (1), Basic Fluid Responsiveness (BFR) is higher when the AM is high and the BM is low (relative to a predetermined neutral threshold). As AM decreases and/or BM increases, BFR decreases. If the BFR is relatively high, for example, a healthcare professional such as physician, and/or the monitor 14 through the fluid delivery device 36, may determine that the patient may benefit from additional fluid, such as saline, plasma, blood, water, any other fluid suitable for delivery to a patient, or any combination thereof. If the BFR is low, the physician may determine that no additional fluid is to be provided to the patient. In short, the BFR allows one to quickly and easily determine whether or not additional fluid should be administered to a patient. Alternatively, the ratio may be inverted to BM/AM, in which case fluid would be administered to a patient when the BFR is low, and fluid is not administered when the BFR is high.

Embodiments allow for a quick and simple determination of fluid responsiveness through analysis of a physiological signal, such as the PPG signal 100. In contrast to previous systems and methods, embodiments may not require an arterial line ("A-line") having a pressure transducer to detect fluid responsiveness. Moreover, embodiments may be used to detect fluid responsiveness with patients that are spontaneously breathing and/or those that are on lung-protective low-tidal volume ventilation, in contrast to numerous previous systems and methods that typically require high-tidal ventilation in order to determine fluid responsiveness.

As explained above, fluid responsiveness may be determined through a ratio of AM/BM of the PPG signal 100. Additionally, as described above, fluid responsiveness may also be determined through a ratio of frequency modulation to baseline modulation of a PPG signal.

Figure 4:
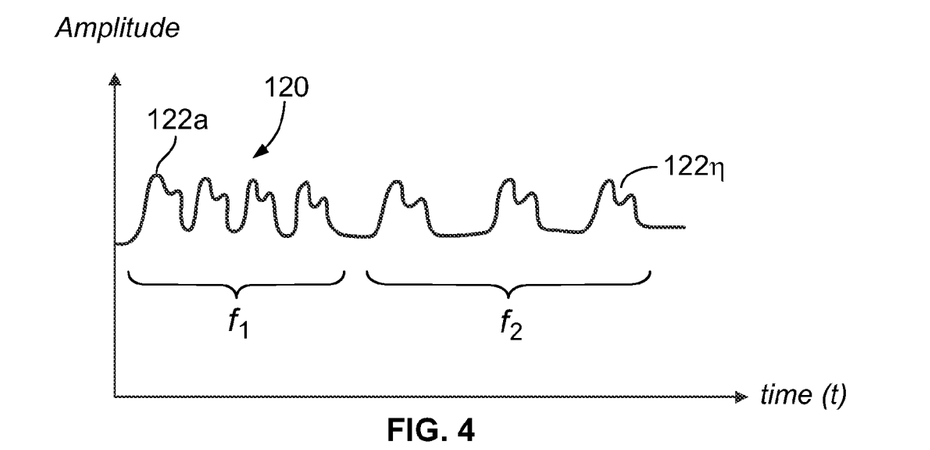
FIG. 4 illustrates a PPG signal over time, according to an embodiment.

FIG. 4 illustrates a PPG signal 120 over time, according to an embodiment. The PPG signal 120 is an example of a physiological signal, but various other physiological signals may be used. The PPG signal 120 includes a plurality of pulses 122a-122n. The frequency of the pulses 122a-122n may vary. For example, the frequency $f_1$ of the pulses 122a-122n over a first period of time may vary from a frequency $f_2$ over a later period of time. The monitor 14 (shown in FIG. 1) may monitor and determine the frequencies $f_1$ and $f_2$. The index-determining module 49 of the monitor 14 may then detect a magnitude of frequency modulation FM over the time period t. The index-determining module 49 of the monitor 14 may determine the FM between neighboring pulses 122a-122n and calculate an aggregate FM over the time period t. Optionally, the index-determining module 49 of the monitor 14 may average the FM between neighboring pulses 122a-122n over the time period t. The index-determining module 49 of the monitor 14 determines the magnitude of FM, which may then be used to determine fluid responsiveness, as explained below.

$$BFR = c(FM/BM) \quad (2)$$

where BFR is Basic Fluid Responsiveness or a fluid responsiveness index, FM is a magnitude of frequency modulation, BM is a magnitude of baseline modulation, and c represents an empirically-determined constant. The empirically-determined constant c may be a calibration value that may be determined through clinical examinations of patients. For example, a group of patients may be monitored to determine fluid responsiveness levels through traditional detection methods, such as with pressure transducers secured to arterial catheters. The traditional detection methods yield fluid responsiveness values that are correlated with particular FM and BM, which may also be monitored at the same time. The empirically-determined calibration coefficient or constant c may then be based on the relation between the fluid responsiveness values and FM and BM. The calibrated value c may then be utilized by the monitor 14 with respect to a determination of basic fluid responsiveness in other patients based on detection of AM and BM. The index-determining module 49 of the monitor 14 may store and use the value c as a calibration coefficient, and/or in relation to a look-up table. Optionally, the BFR may be determined simply through the ratio of FM/BM. Thus, the BFR or fluid responsiveness index may include the ratio of FM/BM and the empirically-determined coefficient c. As shown above, the BFR or fluid responsiveness index may be a product of the ratio of FM/BM and the empirically-determined coefficient c.

The FM may be directly proportional to the stroke volume. For example, FM from respiratory sinus arrhythmia may be directly proportional to stroke volume because heart rate changes to maintain the same cardiac output from reduced stroke volume. Thus, as stroke volume increases, the magnitude of FM may increase. BM may be directly proportional to venous return. Thus, as venous return increases, the magnitude of BM may increase.

The BFR may be a dimensionless scalar index value. Based on Equation (2), Basic Fluid Responsiveness (BFR) is higher when the FM is high and the BM is low (relative to a predetermined neutral threshold). As FM decreases and/or BM increases, BFR decreases. If the BFR is relatively high, a physician may determine that the patient may benefit from additional fluid. If the BFR is low, the physician may determine that no additional fluid is to be provided to the patient. In short, the BFR allows one to quickly and easily determine whether or not additional fluid should be administered to a patient. Alternatively, the ratio may be inverted to BM/FM, in which case fluid would be administered to a patient when the BFR is low, and fluid is not administered when the BFR is high.

Embodiments allow for a quick and simple determination of fluid responsiveness through analysis of the PPG signal 120. In contrast to previous systems and methods, embodiments do not require an arterial line ("A-line") having a pressure transducer to detect fluid responsiveness. Moreover, embodiments may be used to detect fluid responsiveness with patients that are spontaneously breathing and/or those that are on lung-protective low-tidal volume ventilation, in contrast to numerous previous systems and methods that typically require high-tidal ventilation in order to determine fluid responsiveness.

Referring to FIGS. 3 and 4, embodiments provide a system and method of determining fluid responsiveness through analysis of a physiological signal, such as a PPG signal. A fluid responsiveness index may be determined through a ratio of AM/BM, BM/AM, FM/BM, and/or BM/FM. The fluid responsiveness index may be a dimensionless scalar value. A fluid responsiveness index spectrum may range from low, such as 1, to high, such as 10. A physician may determine whether or not additional fluid should be provided to a patient through a review of the fluid responsiveness index. Alternatively, the monitor 14 may automatically determine whether fluid should be provided to a patient through an automated analysis of the fluid responsiveness index. For example, if the fluid responsiveness index is high (such as between 6 and 10), then the physician and/or monitor 14 may determine that the patient should be provided with additional fluid. For example, the monitor 14 may automatically detect the fluid responsiveness index is high, and then automatically provide fluid to the patient through the fluid delivery device 36 (shown in FIG. 1). If the fluid responsiveness signal is low (such as between 1-4), then the physician may refrain from administering additional fluid to the patient.

As noted, the fluid responsiveness index may be determined simply and quickly through an analysis of the PPG signal, without the need for an A-line, or any other sensor (such as an intra-arterial or intra-venous pressure transducer). The system and method may detect a signal through the PPG sensor 12, and analyze the PPG signal to determine AM (and/or FM) and BM to yield a fluid responsiveness index value.

Figure 5:
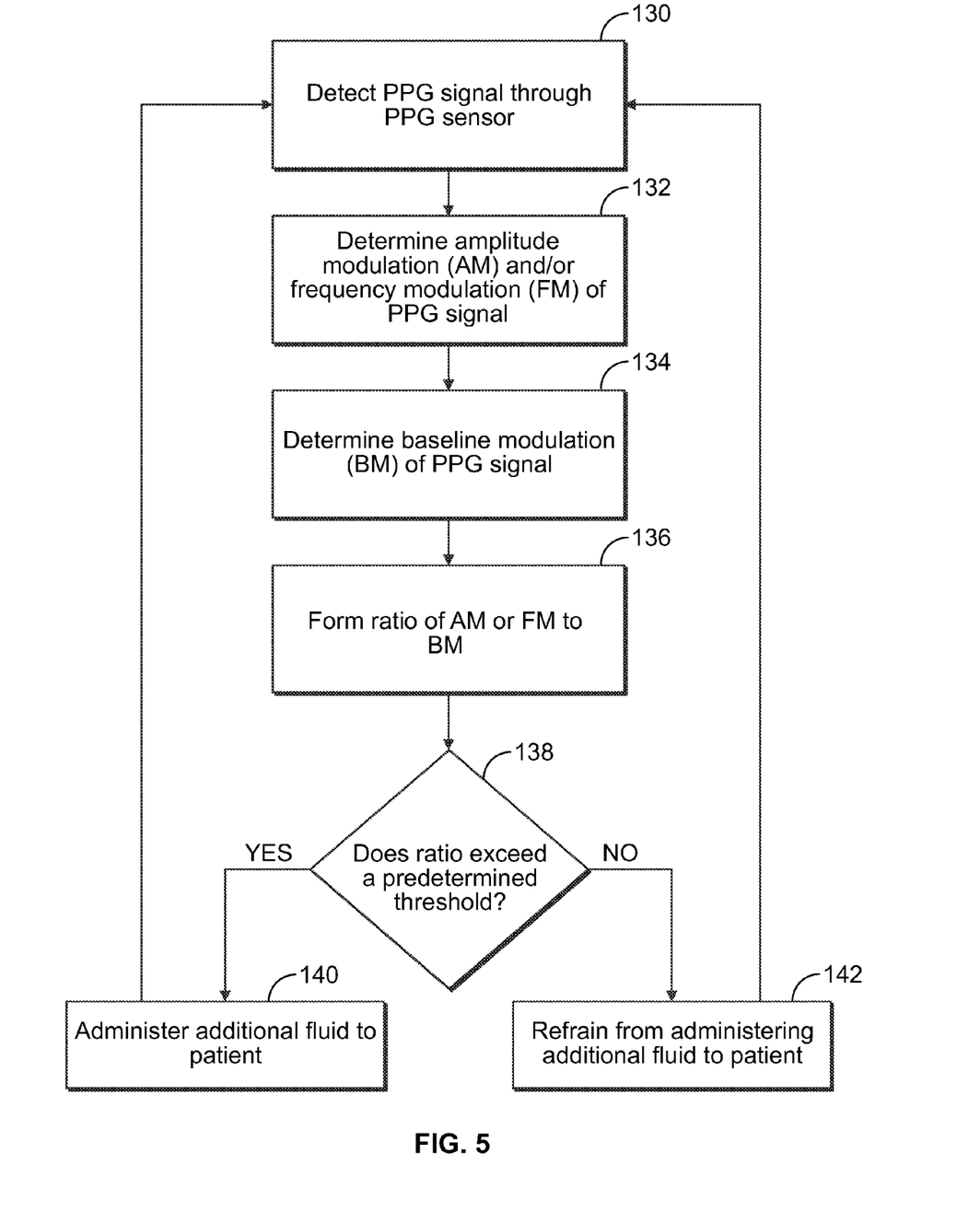
FIG. 5 illustrates a flow chart of a method of determining fluid responsiveness, according to an embodiment.

FIG. 5 illustrates a flow chart of a method of determining fluid responsiveness, according to an embodiment. At 130, the process beings by detecting a PPG signal through a PPG sensor. Then, at 132, the PPG signal is analyzed to determine AM and/or FM. Similarly, at 134, the PPG signal is analyzed to determine BM. Then, at 136, a ratio of (AM or FM)/BM is formed. At 138, a monitor, such as the monitor 14 of FIG. 1, and/or a physician, for example, determines whether the ratio exceeds (or is below) a predetermined threshold. For example, if the index spectrum ranges 1-10, with 1 being low, and 10 being high, the predetermined neutral threshold may be 5. If the index value does exceed the threshold, at 140, additional fluid is administered to the patient. The process then returns to 130. If, however, the index value does not exceed the threshold, at 142, additional fluid is not administered to the patient, and the process returns to 130.

Referring to FIGS. 1-5, the magnitude of respiratory modulation, whether AM, FM, or BM, may also be affected by changes in vascular tone, which relates to the elasticity and hardness of vasculature, such as the arteries. Vascular resistance relates to the resistance to flow that is overcome to push blood through the circulatory system. Arterial compliance, for example relates to a measure of the ability of arteries to allow fluid to pass therethrough.

Vascular tone may vary at different points of the body. For example, the vascular tone at the fingertips, where the PPG sensor 12 (shown in FIG. 1) may be located, may be different than at a location closer to the heart. Ambient temperature and drugs, for example, may affect vascular tone in that both may affect the degree of constriction of the blood vessels.

In cold conditions, for example, peripheral vascular tone may be tight and resistant to blood flow. As the ambient temperature increases, the vascular tone may open and be less resistant to blood flow. If blood vessels are closed and tight, vascular resistance increases, and a reflected pulse is stronger as a greater amount of the reflected pulse is reflected back, as compared to when blood vessels are open and flexible.

Additionally, a PPG signal may be sensitive to motion artifacts. The motion artifacts may be caused by patient and/or PPG sensor movement. Motion artifacts may be caused by hand or finger tremors, coughing, changes in breathing patterns, such as a yawn, a PPG sensor being tugged by a connected cable, and/or the like.

Figure 6:
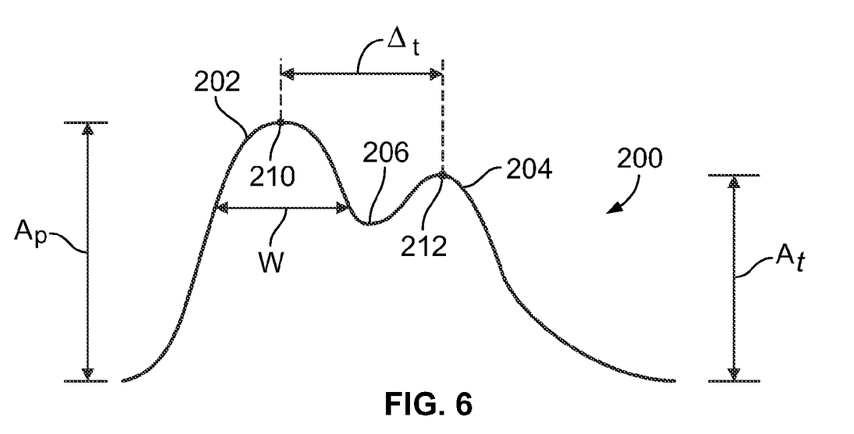
FIG. 6 illustrates a pulse of a PPG signal, according to an embodiment.

FIG. 6 illustrates a pulse 200 of a PPG signal, according to an embodiment. While the pulse 200 is described as a component of a PPG signal, the pulse 200 may be a component of various other physiological signals. The pulse 200 represents a single heartbeat and may include a primary peak 202 separated from a trailing peak 204 by a dichrotic notch 206. The primary peak 202 represents a pressure wave generated from the heart to the point of detection, such as in a finger where the PPG sensor 12 (shown in FIG. 1) is positioned. The trailing peak 204 may represent a pressure wave that is reflected from the location proximate where the PPG sensor 12 is positioned back toward the heart.

The magnitude of AM, BM, and/or FM may be affected by changes in vascular tone and/or motion artifacts. Changes in vascular tone and/or motion artifacts may affect the ratio of AM/BM or FM/BM. Accordingly, changes in the BFR may be due to changes in vascular tone and/or motion artifacts, rather than changes in fluid responsiveness. For example, when arterial compliance in large arteries decreases, the AM of the PPG signal increases relative to the BM due to increased steepening of the propagating pressure wave. When peripheral vascular resistance increases, the AM of the PPG signal may also increase relative to the BM due to peak amplification from an increased reflected pulse.

The BFR or fluid responsiveness index may be corrected or normalized to account for changes in vascular tone and/or motion artifacts through analysis of the PPG signal, as described below. Several metrics of a PPG pulse may be related to arterial compliance, peripheral vascular resistance, and/or motion artifacts.

The normalization module 51 (shown in FIG. 2) of the monitor 14 may compare amplitudes of the peaks 202 and 204 to determine peripheral vasculature resistance. For example, the ratio of the amplitude $A_t$ of the trailing peak 204 to $A_p$ of the primary peak 202 may yield a relative amplitude ratio (RAR).

$$RAR = A_t/A_p \qquad (3)$$

The RAR may be directly proportional to peripheral vascular resistance. Thus, as peripheral vascular resistance increases, $A_t$ increases and/or $A_p$ decreases. Conversely, as peripheral vascular resistance decreases, $A_t$ decreases and/or $A_p$ increases. The RAR provides an indication of peripheral vascular resistance. The normalization module 51 may use the RAR to normalize the fluid responsiveness index, or BFR.

Further, the width W of the primary peak 202 may be directly proportional to arterial compliance. For example, arterial compliance increases with increasing width W. Increased arterial compliance is directly proportional to vascular resistance. Thus, a high degree of arterial compliance yields a low degree of vascular resistance. Conversely, a low degree of arterial compliance yields a high degree of vascular resistance. Therefore, the greater the width W of the primary peak 202, the higher degree of arterial compliance and the lower degree of vascular resistance. The W may be used to normalize the fluid responsiveness index, or BFR. The normalization module 51 may use W to normalize the fluid responsiveness index, or BFR.

Additionally, the time Δt between the primary peak 202 and the trailing peak 204 may be directly proportional to arterial compliance. The time Δt may be measured from a fiducial 210 of the primary peak 202 to a fiducial 212 of the trailing peak 204. The fiducial 210 may be selected as the highest point on the primary peak 202, while the fiducial 212 may be selected as the highest point on the trailing peak 204. However, the fiducials 210 and 212 may be at various other locations on the peaks 202 and 204, respectively. Alternatively, the time Δt may be determined by a time delay between a fiducial on the PPG and another fiducial on: another PPG at a different site (such as a forehead or foot sensor), a phonocardiogram, an electrocardiogram, a pressure transducer on a radial artery, and/or the like.

Because the time Δt may be directly proportional to arterial compliance, as Δt increases, so, too, does arterial compliance. Conversely, as Δt decreases, so too does arterial compliance. The Δt may be used to normalize the fluid responsiveness index, or BFR. The normalization module 51 may measure Δt and use Δt to normalize the fluid responsiveness index, or BFR.

Additionally, a pleth modulation ratio (PMR) may be expressed by AC/DC. The AC physiological component may generally be a variable component related to cardiac synchronous changes in the blood volume with each heartbeat. The AC component is typically superimposed on a constant DC baseline. The PMR may be inversely proportional to vascular resistance. Thus, as PMR increases, vascular resistance decreases. Conversely, as PMR decreases, vascular resistance increases. The PMR may be used to normalize the fluid responsiveness index, or BFR. The normalization module 51 may determine PMR and use PMR to normalize the fluid responsiveness index, or BFR.

The normalization module 51 of the monitor 14 may utilize the RAR, Δt, PMR, and/or W to normalize the BFR or fluid responsiveness index. As shown below, the vascular tone and/or motion artifact corrected fluid responsiveness index (VTC) may be determined as follows:

$$VTC = c(AM/BM \times G/H) \qquad (4)$$

$$VTC = c(FM/BM \times H) \qquad (5)$$

where c is a constant, as described above, AM is Amplitude Modulation, BM is Baseline Modulation, FM is frequency modulation, and G and H may be constants and/or calibration coefficients. As shown above, VTC may be determined through AM/BM or FM/BM. G may be a function of W and/or Δt, while H may be a function of RAR and/or 1/PMR. For example, G may be a calibrated value that is a function of W or Δt, while H may be a calibrated value that is a function of RAR and/or 1/PMR. Optionally, G and H may each be functions of one or more of RAR, Δt, PMR, and/or W.

In an embodiment, G may be directly or inversely proportional to W and/or Δt. In an embodiment, H may directly or inversely proportional to RAR and/or 1/PMR. Each of c, G, and H may be empirically-derived, non-linear functions.

Thus, as shown above, the BFR or fluid responsiveness index may be normalized through calculations of RAR, Δt, PMR, and/or W. The normalization of the BFR or fluid responsiveness index accounts for differences in vascular tone and/or motion artifacts.

The normalization module 51 of the monitor 14 may analyze a plurality of PPG pulses 200 to determine RAR, Δt, PMR, and/or W. For example, a plurality of PPG pulses 200 over a particular time period may be averaged to yield an average pulse, which the normalization module 51 of the monitor 14 analyzes to determine RAR, Δt, PMR, and/or W. Alternatively, the normalization module 51 may analyze each and every pulse over a particular time period to determine RAR, Δt, PMR, and/or W in relation to each and every pulse.

Figure 7:
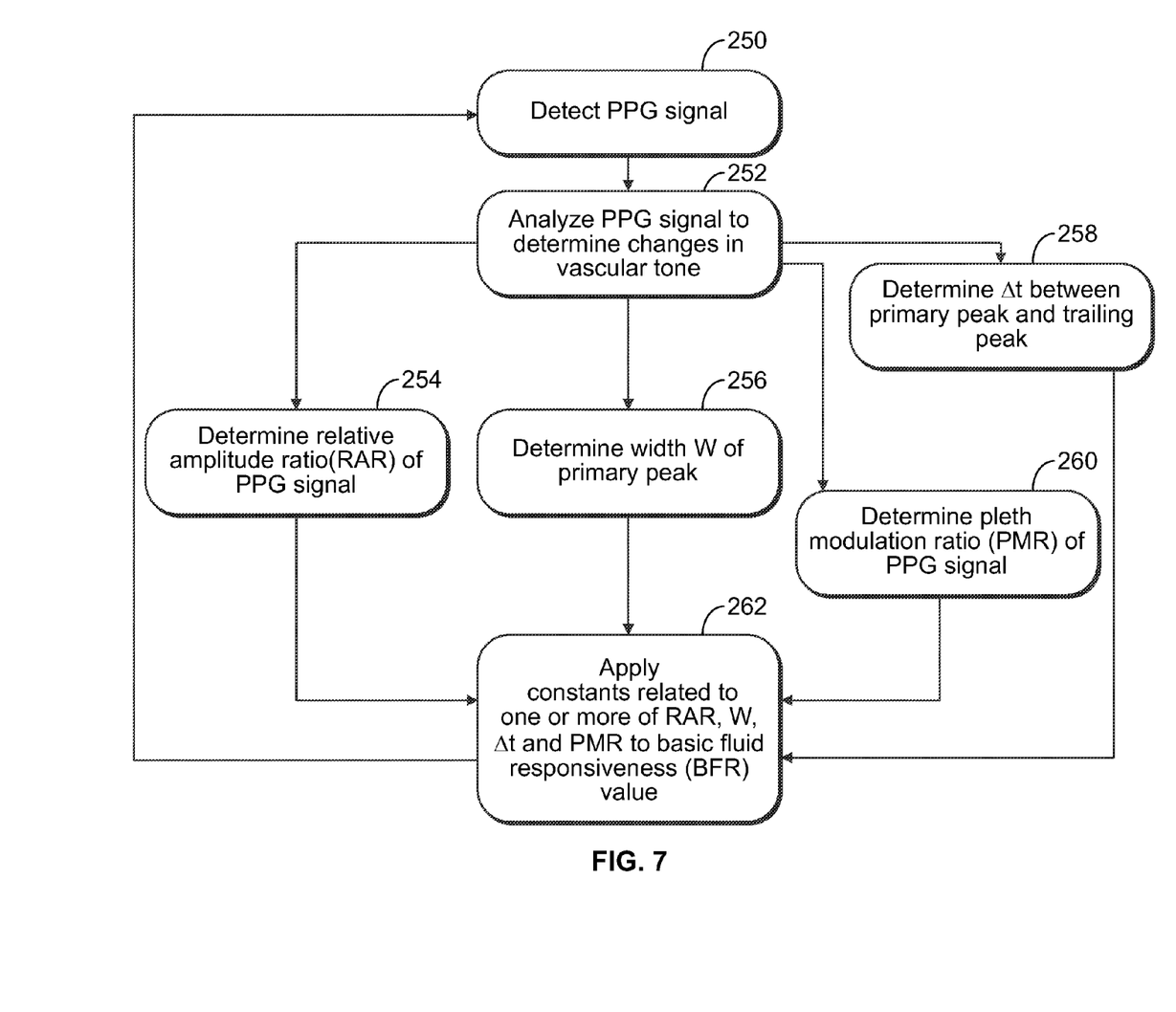
FIG. 7 illustrates a flow chart of a method normalizing a fluid responsiveness index, according to an embodiment.

FIG. 7 illustrates a flow chart of a method normalizing a fluid responsiveness index, according to an embodiment. At 250, a PPG signal is detected, as explained above. At 252, the PPG signal is analyzed to determine changes in vascular tone and/or motion artifacts. Changes in vascular tone, for example may be determined by determining one or more of a relative amplitude ratio (RAR) of the PPG signal at 254, a width W of the primary peak of the PPG signal at 256, Δt between the primary peak and the trailing peak at 258, and/or the pleth modulation ratio (PMR) of the PPG signal at 260. Then, the process continues to 262, in which constants, functions, calibrated values, or the like related to one or more of PAR, W, Δt, and PMR are applied to the basic fluid responsiveness (BFR) value or index in order to normalize the value or index. The process may then return to 250.

It will be understood that the present disclosure is applicable to any suitable physiological signals and that PPG signals are used for illustrative purposes. Those skilled in the art will recognize that the present disclosure has wide applicability to other signals including, but not limited to other physiological signals (for example, electrocardiogram, electroencephalogram, electrogastrogram, electromyogram, heart rate signals, pathological sounds, ultrasound, or any other suitable biosignal) and/or any other suitable signal, and/or any combination thereof.

Various embodiments described herein provide a tangible and non-transitory (for example, not an electric signal) machine-readable medium or media having instructions recorded thereon for a processor or computer to operate a system to perform one or more embodiments of methods described herein. The medium or media may be any type of CD-ROM, DVD, floppy disk, hard disk, optical disk, flash RAM drive, or other type of computer-readable medium or a combination thereof.

The various embodiments and/or components, for example, the control units, modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

As described, embodiments disclose systems and methods for determining a basic fluid responsiveness index or value through analysis of a physiological signal, such as a PPG signal. Embodiments allow for quick and simple determination of fluid responsiveness through analysis of the PPG signal. In contrast to previous systems and methods, embodiments may not require an arterial line ("A-line") having a pressure transducer to detect fluid responsiveness. Moreover, embodiments may be used to detect fluid responsiveness with patients that are spontaneously breathing and/or those that are on lung-protective low-tidal volume ventilation, in contrast to previous systems and methods that typically require high-tidal ventilation in order to determine fluid responsiveness. Further, embodiments provide systems and methods for normalizing a basic fluid responsiveness index or value, such as by accounting for changes in vascular tone and/or motion artifacts.

While various spatial and directional terms, such as top, bottom, lower, mid, lateral, horizontal, vertical, front, and the like may be used to describe embodiments, it is understood that such terms are merely used with respect to the orientations shown in the drawings. The orientations may be inverted, rotated, or otherwise changed, such that an upper portion is a lower portion, and vice versa, horizontal becomes vertical, and the like.

It is to be understood that the above description is intended to be illustrative, and not restrictive. For example, the above-described embodiments (and/or aspects thereof) may be used in combination with each other. In addition, many modifications may be made to adapt a particular situation or material to the teachings without departing from its scope. While the dimensions, types of materials, and the like described herein are intended to define the parameters of the disclosure, they are by no means limiting and are exemplary embodiments. Many other embodiments will be apparent to those of skill in the art upon reviewing the above description. The scope of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

What is claimed is:

1. A system for determining a fluid responsiveness index of a patient from a physiological signal, the system comprising:
   a sensor configured to be secured to an anatomical portion of the patient, wherein the sensor is configured to sense a physiological characteristic of the patient; and
   a monitor operatively connected to the sensor, the monitor configured to receive a physiological signal from the sensor, the monitor comprising an index-determining module configured to determine the fluid responsiveness index through formation of a ratio of one or both of amplitude modulation or frequency modulation of the physiological signal with respect to baseline modulation of the physiological signal.

2. The system of claim 1, wherein the monitor further comprises a normalization module configured to normalize the fluid responsiveness index.

3. The system of claim 2, wherein the normalization module is configured to normalize the fluid responsiveness index to correct for changes in one or both of vascular tone or motion artifacts.

4. The system of claim 2, wherein the normalization module is configured to normalize the fluid responsiveness index based on one or more of a relative amplitude ratio of the physiological signal, a width of at least one primary peak of the physiological signal, a time difference between the at least one primary peak and at least one trailing peak, or a pleth modulation ratio of the physiological signal.

5. The system of claim 1, wherein the index-determining module determines the fluid responsiveness index by applying a calibration coefficient or constant to the ratio.

6. The system of claim 1, wherein the physiological signal comprises a photoplethysmogram (PPG) signal, wherein the sensor comprises a PPG sensor, and wherein the monitor comprises a PPG monitor.

7. The system of claim 1, wherein the sensor comprises a pulse oximetry sensor, and wherein the monitor comprises a pulse oximetry monitor.

8. The system of claim 1, further comprising a fluid delivery device operatively connected to the monitor, wherein the monitor determines whether or not to administer fluid to a patient from the fluid delivery device based on the fluid responsiveness index.

9. A method for determining a fluid responsiveness index of a patient from a physiological signal, the method comprising:
    securing a sensor to an anatomical portion of the patient;
    sensing a physiological characteristic of the patient with the sensor;
    receiving a physiological signal from the sensor at a monitor comprising an index-determining module; and
    determining the fluid responsiveness index with the index-determining module, wherein the determining the fluid responsiveness index operation comprises forming a ratio of one or both of amplitude modulation or frequency modulation of the physiological signal with respect to baseline modulation of the physiological signal.

10. The method of claim 9, further comprising normalizing the fluid responsiveness index with a normalization module, the normalizing operation comprises correcting for changes in one or both of vascular tone or motion artifacts.

11. The method of claim 10, wherein the normalizing operation comprises normalizing the fluid responsiveness index based on one or more of a relative amplitude ratio of the physiological signal, a width of at least one primary peak of the physiological signal, a time difference between the at least one primary peak and at least one trailing peak, or a pleth modulation ratio of the physiological signal.

12. The method of claim 9, further comprising applying a calibration coefficient or constant to the ratio.

13. The method of claim 9, wherein the physiological signal comprises a photoplethysmogram (PPG) signal, wherein the sensor comprises a PPG sensor, and wherein the monitor comprises a PPG monitor.

14. The method of claim 9, further comprising determining whether or not to administer fluid to a patient from a fluid delivery device based on the fluid responsiveness index.

15. A tangible and non-transitory computer readable medium that includes one or more sets of instructions configured to direct a computer to:
    receive a physiological signal from a sensor secured to an anatomical portion of a patient; and
    determine a fluid responsiveness index of a patient by forming a ratio of one or both of amplitude modulation or frequency modulation of the physiological signal with respect to baseline modulation of the physiological signal.

16. The tangible and non-transitory computer readable medium of claim 15, further configured to direct the computer to normalize the fluid responsiveness index with a normalization module by correcting for changes in one or both of vascular tone or motion artifacts.

17. The tangible and non-transitory computer readable medium of claim 16, further configured to direct the computer to normalize the fluid responsiveness index based on one or more of a relative amplitude ratio of the physiological signal, a width of at least one primary peak of the physiological signal, a time difference between the at least one primary peak and at least one trailing peak, or a pleth modulation ratio of the physiological signal.

18. The tangible and non-transitory computer readable medium of claim 15, further configured to direct the computer to apply a calibration coefficient or constant to the ratio.

19. The tangible and non-transitory computer readable medium of claim 15, wherein the physiological signal comprises a photoplethysmogram (PPG) signal.

20. The tangible and non-transitory computer readable medium of claim 15, further configured to direct the computer to determine whether or not to administer fluid to a patient from a fluid delivery device based on the fluid responsiveness index.

* * * * *